US008911492B2

(12) United States Patent
Zhao

(10) Patent No.: US 8,911,492 B2
(45) Date of Patent: Dec. 16, 2014

(54) COATING FOR A MEDICAL DEVICE HAVING AN ANTI-THROMBOTIC CONJUGATE

(71) Applicant: Cordis Corporation, Bridgewater, NJ (US)

(72) Inventor: Jonathon Z. Zhao, Belle Mead, NJ (US)

(73) Assignee: Cordis Corporation

( * ) Notice: Subject to any disclaimer, the term of this patent is extended or adjusted under 35 U.S.C. 154(b) by 143 days.

(21) Appl. No.: 13/751,997

(22) Filed: Jan. 28, 2013

(65) Prior Publication Data

US 2013/0172986 A1    Jul. 4, 2013

Related U.S. Application Data

(62) Division of application No. 11/741,997, filed on Apr. 30, 2007, now Pat. No. 8,383,156.

(51) Int. Cl.
| | | |
|---|---|---|
| *A61F 2/00* | (2006.01) | |
| *A61K 9/14* | (2006.01) | |
| *A61F 2/06* | (2013.01) | |
| *C09D 133/14* | (2006.01) | |
| *A61L 33/08* | (2006.01) | |
| *A61L 31/10* | (2006.01) | |
| *A61L 31/16* | (2006.01) | |
| *A61F 2/91* | (2013.01) | |

(52) U.S. Cl.
CPC ............ *A61F 2/0077* (2013.01); *C09D 133/14* (2013.01); *A61L 2300/42* (2013.01); *A61L 33/08* (2013.01); *A61F 2/91* (2013.01); *A61F 2250/0068* (2013.01); *A61L 31/10* (2013.01); *A61L 31/16* (2013.01)
USPC .......................... 623/1.43; 424/423; 424/486

(58) Field of Classification Search
None
See application file for complete search history.

(56) References Cited

U.S. PATENT DOCUMENTS

| | | | |
|---|---|---|---|
| 5,525,348 | A | 6/1996 | Whitbourne et al. |
| 5,837,313 | A | 11/1998 | Ding et al. |
| 5,855,618 | A | 1/1999 | Patniak |
| 6,245,753 | B1 | 6/2001 | Byun et al. |
| 6,258,121 | B1 | 7/2001 | Yang |
| 6,461,665 | B1 | 10/2002 | Scholander |
| 6,559,132 | B1 | 5/2003 | Holmer |
| 6,702,850 | B1 * | 3/2004 | Byun et al. ................ 623/1.44 |
| 6,764,507 | B2 | 7/2004 | Shanley et al. |
| 6,767,405 | B2 | 7/2004 | Eketorp et al. |
| 7,129,224 | B1 | 10/2006 | Byun et al. |
| 2004/0249449 | A1 | 12/2004 | Shanley et al. |
| 2005/0191333 | A1 | 9/2005 | Hsu et al. |
| 2006/0204533 | A1 | 9/2006 | Hsu et al. |

FOREIGN PATENT DOCUMENTS

| | | |
|---|---|---|
| EP | 0832618 B1 | 4/1998 |
| WO | 2005097223 A1 | 10/2005 |
| WO | 2006099514 A2 | 9/2006 |

OTHER PUBLICATIONS

Lee, Jung Seok, Heparin conjugated polymeric micelle for long-term delivery of basic fibroblast growth factor, Journal of Controlled Release, 117 (2007) pp. 204-209.*
Breitenbach, Armin et al., Biodegradable comb polyesters: Part 1 Synthesis, Characterization and structural analysis of poly(lactide) and poly(lactide-co-glycolide) grafted onto water soluble poly(vinyl alcohol) as backbone, Polymer vol. 39 No. 14 (1998) pp. 3261-3271.*
Wiggins, Jeffrey S., Hydrolytic degradation of poly(D,L-lactide) as a function of end groups: Carboxylic acid vs. Hydroxyl, Polymer 47 (2006) pp. 1960-1969.*
European Search Report Jan. 14, 2011 for corresponding EP Patent Application No. EP 10187104.
Song, C., et al., "Arterial uptake of biodegradable nanoparticles for intravascular local drug delivery: Results with an acute dog model," Journal of Controlled Release, 1998, pp. 201-211, vol. 54.
Westedt, R., et al. "Poly(vinyl alcohol)-graft-poly(lactide-co-glycolide) Nanoparticles for Local Delivery of Paclitaxel for Restenosis Treatment," Journal of Controlled Release, vol. 119, (2007) pp. 41-51.
Llanos, G., et al. "Heparin-poly(ethylene glycol)-poly(vinyl Alcohol) Hydrogel: Preparation and Assessment of Thrombogenicity," Biomaterials, vol. 13, No. 7 (1992) pp. 421-424.
Marconi, W., et al. "Covalent bonding of Heparin to a Vinyl Copolymer for Biomedical Applications", Biomaterials, vol. 18, No. 12 (1997) pp. 885-890.
European Search Report dated Jan. 21, 2011 for corresponding Application No. EP 10187100.2-1219/2272549.
Jagur-Grodzinski, J., "Biomedical Application of Functional Polymers," Reactive &Functional Polymers, vol. 39, No. 2 (1999) pp. 99-138.
European Search Report dated Nov. 24, 2008 for corresponding EP Patent Application No. 08251419.1-1219/1987851.

* cited by examiner

*Primary Examiner* — Scott Long
*Assistant Examiner* — Lyndsey Beckhardt

(57) ABSTRACT

An implantable device having a coating comprising a comb-type anti-thrombotic conjugate to prevent or reduce the formation of thrombosis on the surface of the device. The device includes a frame expandable from a first diameter to a second diameter wherein the frame has an inner surface and an outer surface, a plurality of structural features disposed along the frame and a plurality of polymer anti-thrombotic conjugate particles situated with the plurality of structural features. The particle can be created utilizing the comb type polymer and heparin conjugate as a carrier for a therapeutic agent within its polymer matrix. The structural features allow for particles having differing properties to be placed at various locations along the device. Moreover, particles having at least two different agents can be located within the same structural feature.

9 Claims, 6 Drawing Sheets

COATING FOR A MEDICAL DEVICE HAVING AN ANTI-THROMBOTIC CONJUGATE

CROSS-REFERENCE TO RELATED APPLICATIONS

This application is a divisional application of Ser. No. 11/741,997 filed Apr. 30, 2007, which is incorporated herein by reference in its entirety.

FIELD OF INVENTION

The present invention relates to a material for application to at least a portion of the surface of an article or for implantation within an article. In particular, this invention relates to a comb type bioabsorbable polymer having an anti-thrombotic composition conjugated therewith wherein an anti-restenotic agent may be contained within the polymer matrix of the bioabsorbable polymer. This invention also relates to a device having the conjugate coated to its surface or contained within the device itself.

BACKGROUND OF INVENTION

Stenosis is the narrowing or constriction of a vessel resulting from the buildup of fat, cholesterol, and other substances over time. In severe cases, stenosis can completely occlude a vessel. Interventional procedures have been employed to open stenosed vessels. One example of an interventional procedure is percutaneous transluminal coronary angioplasty (PTCA) or balloon coronary angioplasty. In this procedure, a balloon catheter is inserted and expanded in the constricted portion of the vessel for clearing a blockage. About one-third of patients who undergo PTCA suffer from restenosis, wherein the vessel becomes blocked again, within about six months of the procedure. Thus, restenosed arteries may have to undergo another angioplasty. In order to avoid additional PTCA implantable medical devices such as stents have been placed within the vessel following PTCA or in lieu of PTCA. Nonetheless, restenosis may still result even with the implantation of a stent.

Restenosis can be inhibited by a common procedure that consists of inserting a stent into the effected region of the artery instead of, or along with, angioplasty. A stent is a tube made of metal or plastic, which can have either solid walls or mesh walls. Most stents in use are metallic and are either self-expanding or balloon-expandable. The decision to undergo a stent insertion procedure depends on certain features of the arterial stenosis. These include the size of the artery and the location of the stenosis. The function of the stent is to buttress the artery that has recently been widened using angioplasty, or, if no angioplasty was used, the stent is used to prevent elastic recoil of the artery. Stents are typically implanted via a catheter. In the case of a balloon-expandable stent, the stent is collapsed to a small diameter and slid over a balloon catheter. The catheter is then maneuvered through the patient's vasculature to the site of the lesion or the area that was recently widened. Once in position, the stent is expanded and locked in place. The stent stays in the artery permanently, holds it open, improves blood flow through the artery, and relieves symptoms (usually chest pain).

Stents are not completely effective in preventing restenosis at the implant site. Restenosis can occur over the length of the stent and/or past the ends of the stent. Physicians have recently employed new types of stents that are coated with a thin polymer film loaded with a drug that inhibits smooth cell proliferation. The coating is applied to the stent prior to insertion into the artery using methods well known in the art, such as a solvent evaporation technique. The solvent evaporation technique entails mixing the polymer and drug in a solvent. The solution comprising polymer, drug, and solvent can then be applied to the surface of the stent by either dipping or spraying. The stent is then subjected to a drying process, during which the solvent is evaporated, and the polymeric material, with the drug dispersed therein, forms a thin film layer on the stent.

The release mechanism of the drug from the polymeric materials depends on the nature of the polymeric material and the drug to be incorporated. The drug diffuses through the polymer to the polymer-fluid interface and then into the fluid. Release can also occur through degradation of the polymeric material. The degradation of the polymeric material may occur through hydrolysis or an enzymatic digestion process, leading to the release of the incorporated drug into the surrounding tissue.

An important consideration in using coated stents is the release rate of the drug from the coating. It is desirable that an effective therapeutic amount of the drug be released from the stent for a reasonably long period of time to cover the duration of the biological processes following and an angioplasty procedure or the implantation of a stent. Burst release, a high release rate immediately following implantation, is undesirable and a persistent problem. While typically not harmful to the patient, a burst release "wastes" the limited supply of the drug by releasing several times the effective amount required and shortens the duration of the release period. Several techniques have been developed in an attempt to reduce burst release. For example, U.S. Pat. No. 6,258,121 B1 to Yang et al. discloses a method of altering the release rate by blending two polymers with differing release rates and incorporating them into a single layer.

A potential drawback associated with the implantation of a drug eluting stent (DES) is that thrombosis may occur at different times following implantation or deployment. Thrombosis is the formation of blood clots on or near an implanted device in the blood vessel. The clot is usually formed by an aggregation of blood factors, primarily platelets and fibrin, with entrapment of cellular elements. Thrombosis, like stenosis, frequently causes vascular obstruction at the point of its formation. Both restenosis and thrombosis are two serious and potentially fatal conditions that require medical intervention. A thrombus formation on the surface of a stent is frequently lethal, leading to a high mortality rate of between 20 to 40% in the patients suffering from a thrombosis in a vessel.

Although effective in reducing restenosis, some of the components of the coatings utilized to prevent restenosis may increase the risk of thrombosis. Drug eluting stents are typically not associated with an increase of acute and subacute thrombosis (SAT), or a medium term thrombosis (30 days after stent implantation) following a stent implantation. Long term clinical follow up studies, however, suggest that these devices may be involved with increased incident rates of very long term thrombosis (LST). Although the increase of LST has been found to be less than 1%, a high mortality rate is usually associated with LST. One way to prevent this is to include a coating of an anti-coagulant, such as heparin, on the device.

One way to address the formation of stent thrombosis is through the use of a anticoagulant such as a heparin. Heparin is a substance that is well known for its anticoagulation ability. It is known in the art to apply a thin polymer coating loaded with heparin onto the surface of a stent using the solvent evaporation technique. For example, U.S. Pat. No. 5,837,313 to Ding et al. describes a method of preparing a heparin coating composition. A drawback to the use of heparin, however is that it does not co-exist well with agents that prevent restenosis. For example, if heparin is mixed with an anti-thrombotic agent within a polymer coating, the hydrophilic nature of heparin will interfere with the desired elution profile for the anti-restenotic agent. For example, therapeutic agent is embedded in the matrix of a polymer coating by solvent processing. If an anti-coagulant is also embedded in the polymer matrix, it will attract water in an uncontrolled manner. This can happen during manufacturing or when the coated device is implanted and will adversely affect the stability or efficacy of the agent and/or interfere with the desired elution profile.

Nonetheless, several approaches have been proposed for combining anti-thrombotic and therapeutic agents within the coatings for an implantable medical device. U.S. Pat. No. 5,525,348—Whitbourne discloses a method of complexing pharmaceutical agents (including heparin) with quarternary ammonium components or other ionic surfactants and bound with water insoluble polymers as an antithrombotic coating composition. This method suffers from the possibility of introducing naturally derived polymer such as cellulose, or a derivative thereof, which is heterogeneous in nature and may cause unwanted inflammatory reactions at the implantation site. These ionic complexes between an antithrombotic agent such as heparin and an oppositely charged carrier polymer may also negatively affect the coating integration, and if additional pharmaceutical agents are present, may affect the shelf stability and release kinetics of these pharmaceutical agents.

A slightly different approach is disclosed in U.S. Pat. No. 6,702,850, 6,245,753, and U.S. Pat. No. 7,129,224—Byun wherein antithrombotic agents, such as heparin, are covalently conjugated to a non-absorbable polymer, such as a polyarylic acid, before use in a coating formulation. The overall hydrophobicity of these conjugates is further adjusted by addition of a hydrophobic agent such as octadecylamine, which is an amine with a long hydrocarbon chain. This approach has several potential disadvantages such as the known toxicity of polyacrylic acid after heparin is metabolized in vivo. The addition of a hydrophobic amine also raises the concern of tissue compatibility and reproduction of the substitution reactions of each step. Moreover, the remaining components of the coating are not biodegradable.

Another antithrombotic coating approach is disclosed in U.S. Pat. No. 6,559,132—Holmer, U.S. Pat. No. 6,461,665—Scholander, and U.S. Pat. No. 6,767,405—Eketrop whereby a carrier molecule such as chitosan is conjugated to an activated metal surface of a medical device. Thereafter, heparin is covalently conjugated to an intermediate molecule. This process may be repeated several times until a desired antithrombotic layer is achieved. Alternatively, this coating can be achieved in a batch process mode. This approach, however, is not readily applicable to a medical device that is coated with a polymer coating that contains pharmaceutical agent/s. Some of these successful anti-restenotic agents such as sirolimus may be damaged during these conjugating processes, especially these processes where aqueous processes are involved.

PCT application WO2005/097223 A1—Stucke et al, discloses a method wherein a mixture of heparin conjugated with photoactive crosslinkers with dissolved or dispersed with other durabal polymers such as Poly(butyl methacrylate) and poly(vinyl pyrrolidone) in a same coating solution and crosslinked with UV light in the solution or after the coating is applied. The potential disadvantage of this approach is that the incorporated drug/s may be adversely affected by the high energy UV light during crosslinking process, or worse, the drug/s may be crosslinked to the matrix polymers if they possess functional groups that may be activated by the UV energy.

Another general approach as disclosed in US 2005/0191333 A1, US 2006/0204533 A1, and WO 2006/099514 A2,—all by Hsu, Li-Chien, et al., uses a low molecular weight complex of heparin and a counter ion (stearylkonium heparin), or a high molecular weight polyelectrolyte complex, such as dextran, pectin to form a complex form of an antithrombotic entity. These antithrombotic complexes are further dispersed in a polymer matrix that may further comprise a drug. Such approaches create a heterogeneous matrix of a drug and a hydrophilic species of heparin wherein the hydrophilic species attract water before and after the implantation to adverse the stability and release kinetics of the drug. In addition, the desired antithrombotic functions of heparin and similar agent should be preferably located on the surface, not being eluted away from the surface of a coated medical device.

Thus, there remains a need for a coating material that can satisfy the stringent requirements, as described above, for applying on at least one surface of a medical device and can be prepared through a process that is compatible with the sensitive pharmaceutical or therapeutic agents impregnated in the coatings. This helps to fill a need for a coating that treats both restenosis and prevents thrombosis when applied to the outer surface of a drug eluting stent.

SUMMARY OF THE INVENTION

A conjugate between a heparin and a comb type bioabsorbable polymer with a free carboxyl end group and a device having the conjugate applied to its surface or embedded within its structure is provided. The outmost layer of the coating comprises the conjugate of the present invention, which prevents the formation of thrombosis, and also serves to modulate the release kinetics of the agent(s) contained within an inner layer(s) of the coating.

A first or sub-layer of the coating is prepared by mixing a polymeric material and a biologically active agent with a solvent, thereby forming a homogeneous solution. The polymeric material can be selected from a wide range of synthetic materials, but in one exemplary embodiment, a poly(lactide-to-glycolide) (PLGA) is used. The biologically active agent is selected depending on the desired therapeutic results. For example, an antiproliferative drug such as paclitaxel, an immunosuppressant, such as a rapamycin, and/or anti-inflammatory drug, such as dexamethasone, may be included in the inner layer. Once prepared, the solution can be applied to the device through a dipping or spraying process. During drying, the solvent evaporates, and a thin layer of the polymeric material loaded with the biologically active agent is left coated over the stent. It should be noted that the current invention is not limited to just one inner layer or biologically active agent per layer. It is within the scope of this invention to add one or more distinct biologically active agents to each layer and/or have more than one inner layer loaded with a biologically active agent.

The second or outer layer comprises an anti-thrombotic heparin-bioabsorbable polymer conjugate. This coating may be applied over the inner drug-containing layers using, for example, a dip coating or spray coating process. In one exemplary embodiment of the present invention, the outer layer comprising an anti-thrombotic heparin-bioabsorbable polymer conjugate that may be dissolved in a mixed solvent system comprising ethyl acetate (EA) and isopropanol (IPA). The solution is then sprayed onto the surface of the device that has already been coated with the agent-containing layer as described above. After drying, the anti-thrombotic heparin bioabsorbable polymer conjugate remains in the outer layer of the coating, allowing agent from the inner layer to be eluted there through.

The coated device is inserted into an afflicted area of a body, for example, a vessel like the coronary artery, using an appropriate procedure that depends on the properties of the device. Once in place, the device will hold the vessel open. The biologically active agent will be released from the first layer, thereby providing the desired therapeutic result, such as inhibiting smooth cell proliferation. The anti-thrombotic heparin-bioabsorbable polymer conjugate in the outmost layer becomes partially hydrated and prevents blood coagulation on and around the device, thus inhibiting thrombosis and sub-acute device thrombosis. In addition, the anti-thrombotic heparin-bioabsorbable polymer conjugate in the outmost layer may additionally reduce or prevent the burst release of the biologically active agent from the inner drug containing layer, thereby allowing the release to occur over a relatively extended period of time.

Alternatively, a particle can be created utilizing the comb type polymer and heparin conjugate as a carrier for a therapeutic agent within its polymer matrix. In this embodiment the agent is somewhat associated with the hydrophobic core of the comb polymer. The agent is co-dissolved with the conjugate using a solvent that is later evaporated creating particles with the agent at their core. These particles are ideally suited for placement within the structure of a device. For example, a device may have structural features such as wells, indentations, folds, or channels having particles therein. This allows for particles having differing properties to be placed at various locations along the device. Moreover, particles having at least two different agents can be located within the same structural feature. Agent is released from the structural feature as the particles degrade. Simultaneously, the presence of heparin will prevent thrombosis at the placement site of the device.

DESCRIPTION OF THE DRAWINGS

The features and advantages of the invention will be apparent to those of ordinary skill in the art from the following detailed description of which.

DETAILED DESCRIPTION OF THE INVENTION

Figure 1:
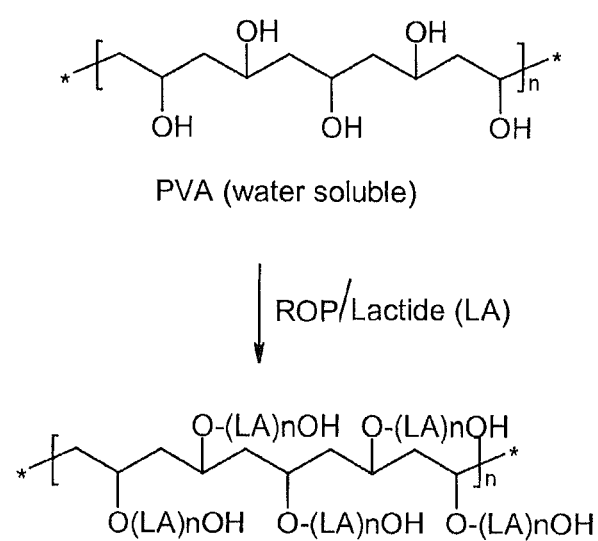
FIG. 1 is a schematic representation of a ring opening polymerization of a lactone dimer (lactide) with polyvinyl alcohol (PVA) as the initiator that forms a comb type polymer.

One or more layers of polymeric compositions are applied to a medical device to provide a coating thereto or are loaded within a structural feature of the medical device. The polymeric compositions perform differing functions. For example, one layer may comprise a base coat that allows additional layers to adhere thereto. An additional layer(s) can carry bioactive agents within their polymer matrices. Alternatively, a single coat may be applied wherein the polymeric composition is such that the coat performs multiple functions, such as allowing the coating to adhere to the device and housing an agent that prevents thrombosis. Other functions include housing an agent to prevent restenosis.

The chemical nature of an agent can limit the number of agents that a coating may carry. For example, an antithrombotic agent tends to be hydrophilic while an anti-proliferative agent tends to be comparatively hydrophobic. Hence, it is desired to entrap a hydrophobic agent within the matrix of a polymer coating to limit its exposure to water and control its elution from the matrix. The present invention supports two agents having differing properties in close proximity by providing a conjugate between an anti-coagulant such as heparin and a bioabsorbable polymer with a free carboxyl end group. This configuration will result in the hydrophilic heparin agent being oriented substantially away from the hydrophobic agent that resides within the polymer matrix. Thus, when applied to a medical device the coating having the conjugate ensures that the anti-thrombotic agent is substantially oriented away from any hydrophobic agents that may be contained within the polymer matrix.

The following definitions are provided for ease of understanding the present invention and should not be construed as limiting the description of then invention in any way.

As used herein, "stent" means a generally tubular structure constructed from any biocompatible material that is inserted into a conduit to keep the lumen open and prevent closure due to a stricture or external compression.

As used herein, "biologically active agent" means a drug or other substance that has therapeutic value to a living organism including without limitation antithrombotics, anticancer agents, anticoagulants, antiplatelet agents, thrombolytics, antiproliferatives, anti-inflammatories, agents that inhibit restenosis, smooth muscle cell inhibitors, antibiotics, and the like, and/or mixtures thereof and/or any substance that may assist another substance in performing the function of providing therapeutic value to a living organism.

Exemplary anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmetteguerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

Exemplary antiinflammatory drugs include classic nonsteroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof; COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof; and mixtures thereof.

As used herein, "effective amount" means an amount of pharmacologically active agent that is nontoxic but sufficient to provide the desired local or systemic effect and performance at a reasonable benefit/risk ratio attending any medical treatment.

Figure 3:
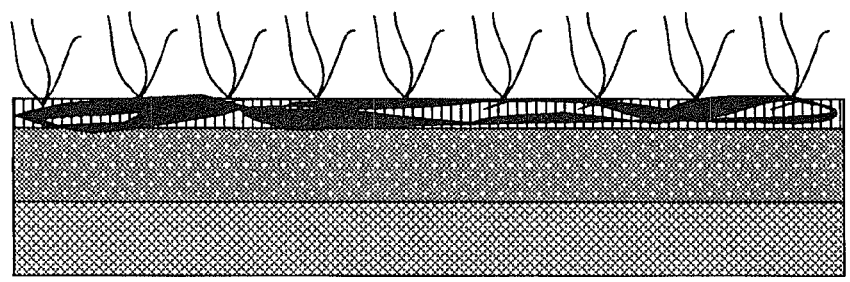
FIG. 3 is a schematic of a coating having the biodegradable comb type polyester heparin conjugate of the present invention present in an outer layer applied to the surface of a device.

FIG. 3 illustrates an exemplary embodiment of a coating(s) of the present invention applied a surface 2. The surface 2 is located on, for example, an implantable medical device. The coating comprises a first or inner layer 4 of polymeric film loaded with a biologically active agent that, for example, prevents smooth cell proliferation and migration. First layer or coating 4 may contain more than one biologically active agent.

One manner in which the agent is placed within the matrix of the polymer involves using a solvent or mixture of solvents whereby the agent and polymer are dissolved therein. As the mixture dries, the solvent is removed leaving the agent entrapped within the matrix of the polymer. Exemplary polymers that can be used for making the inner/first polymeric layer include polyurethanes, polyethylene terephthalate (PET), PLLA-poly-glycolic acid (PGA) copolymer (PLGA), polycaprolactone (PCL) poly-(hydroxybutyrate/hydroxyvalerate) copolymer (PHBV), poly(vinylpyrrolidone) (PVP), polytetrafluoroethylene (PTFE, Teflon®), poly(2-hydroxyethylmethacrylate) (poly-HEMA), poly(etherurethane urea), silicones, acrylics, epoxides, polyesters, urethanes, parlenes, polyphosphazene polymers, fluoropolymers, polyamides, polyolefins, and mixtures thereof. Exemplary bioabsorbable polymers that can be used for making the inner/first polymeric film include polycaprolactone (PCL), poly-D, L-lactic acid (DL-PLA), poly-L-lactic acid (L-PLA), poly(hydroxybutyrate), polydioxanone, polyorthoester, polyanhydride, poly(glycolic acid), polyphosphoester, poly (amino acids), poly(trimethylene carbonate), poly(iminocarbonate), polyalkylene oxalates, polyphosphazenes, and aliphatic polycarbonates.

A second or outmost layer 6 may comprise an anti-thrombotic heparin-bioabsorbable polymer conjugate with strong anticoagulation properties. The second layer of anti-thrombotic heparin-bioabsorbable polymer conjugate may additionally have the effect of preventing a burst release of the biologically active agent dispersed in the first or inner 4 layer, resulting in a relatively longer release period of the layer 4 may contain more than one biologically active agent. In addition, the conjugate 6 orients the hydrophilic heparin 8 substantially away from the hydrophobic inner layer 4.

For purposes of illustrating the present invention, the coating(s) are applied to a medical device such as stents and/or stent-graft. In general, stents are made from metal such as those manufactured from stainless steel or cobalt chromium alloys. Stents may, however, also be manufactured from polymeric materials. It is also to be understood that any substrate, medical device, or part thereof having contact with organic fluid, or the like, may also be coated with the present invention. For example, other devices such as vena cava filters and anastomosis devices may be used with coatings having agents therein or the devices themselves may be fabricated with polymeric materials that have the drugs contained therein. Any of the stents or other medical devices described herein may be utilized for local or regional drug delivery. Balloon expandable stents may be utilized in any number of vessels or conduits, and are particularly well suited for use in coronary arteries. Self-expanding stents, on the other hand, are particularly well suited for use in vessels where crush recovery is a critical factor, for example, in the carotid artery.

It is desirable, but not required, that the first 4 and second 6 coatings or layers cover at least a portion of the entire stent surface 2. The application of the first layer 4 is accomplished through a solvent evaporation process or some other known method such as solvent cast spray coating. The solvent evaporation process entails combining the polymeric material and the biologically active agent with a solvent, such as tetrahydrofuran (THF), which are then stirred to form a mixture. An illustrative polymeric material of the first layer comprises polyurethane and an illustrative biologically active agent comprises a rapamycin. The mixture is applied to the surface 2 of the stent by either spraying the solution onto the stent; or dipping the stent into the solution. After the mixture has been applied, the stent is subjected to a drying process, during which, the solvent evaporates and the polymeric material and biologically active agent form a thin film on the stent. Alternatively, a plurality of biologically active agents can be added to the first layer 4.

The second or outmost layer 6 of the stent coating comprises an anti-thrombotic heparin-bioabsorbable polymer conjugate. The anti-thrombotic heparin-bioabsorbable polymer conjugate may be soluble in organic solvents or mixtures of organic solvents of varying polarity. The heparin 8 may comprise an unfracationated heparin, fractionated heparin, a low molecular weight heparin, a desulfated heparin and heparins of various mammalian sources. Exemplary anti-thrombotic agents may include: Vitamin K antagonist such as Acenocoumarol, Clorindione, Dicumarol (Dicoumarol), Diphenadione, Ethyl biscoumacetate, Phenprocoumon, Phenindione, Tioclomarol, Warfarin; Heparin group anti-platelet aggregation inhibitors such as Antithrombin III, Bemiparin, Dalteparin, Danaparoid, Enoxaparin, Heparin, Nadroparin, Parnaparin, Reviparin, Sulodexide, Tinzaparin; other platelet aggregation inhibitors such as Abciximab, Acetylsalicylic acid (Aspirin), Aloxiprin, Beraprost, Ditazole, Carbasalate calcium, Cloricromen, Clopidogrel, Dipyridamole, Eptifibatide, Indobufen, Iloprost, Picotamide, Prasugrel, Prostacyclin, Ticlopidine, Tirofiban, Treprostinil, Triflusal; enzymatic anticoagulants such as Alteplase, Ancrod, Anistreplase, Brinase, Drotrecogin alfa, Fibrinolysin, Protein C, Reteplase, Saruplase, Streptokinase, Tenecteplase, Urokinase; direct thrombin inhibitors such as Argatroban, Bivalirudin, Dabigatran, Desirudin, Hirudin, Lepirudin, Melagatran, Ximelagatran; and other antithrombotics such as Dabigatran, Defibrotide, Dermatan sulfate, Fondaparinux, Rivaroxaban.

Figure 2:
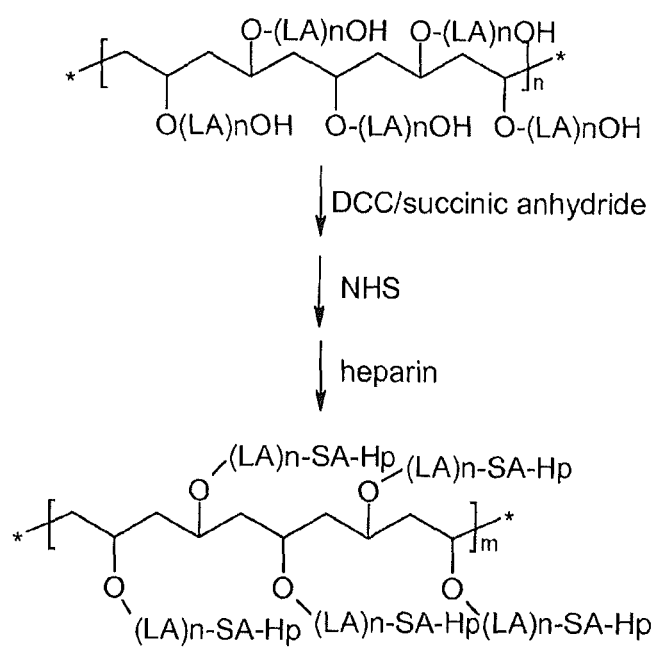
FIG. 2 is a schematic representation of the conjugation of heparin to PVA-initiated PLA comb type biodegradable polymer.

As shown in FIGS. 1 and 2, an exemplary anti-thrombotic heparin-biocompatible copolymer conjugate is prepared as follows. First, as shown in FIG. 1, a cyclic dimer of d,l-lactide, is polymerized at elevated temperature of about 140 C, in the presence of a catalyst Stannous Octoate $(Sn(Oct)_2$ and a predetermined amount of poly(vinyl alcohol) (PVA, sufficiently hydrolyzed to be water soluble) as the ring opening initiator. Ring opening polymerization results in an end product that contains a homopolymer of polyester with hydroxyl end groups. The molecular weight of each polymer is determined by the ratio between the cyclic dimer and the PVA initiator. The higher the ratio between the cyclic dimer to the initiator, the higher the molecular weight of the copolymer of PVA-PLA.

In one embodiment of the present invention the hydroxyl groups at one end of the final PVA-PLA copolymer may be further converted to a carboxyl group that may be employed in the subsequent conjugation reaction with a heparin molecule. Although any heparin molecule, a recombinant heparin, heparin derivatives or heparin analogues (having a preferred weight of 1,000-1,000,000 daltons) may be used in the coupling reaction to make the final anti-thrombotic heparin-bioabsorbable polymer conjugate, it is preferred to use a desulfated heparin to increase the coupling efficiency of the reaction.

Once the anti-thrombotic heparin-bioabsorbable polymer conjugate is prepared, the second layer comprising the anti-thrombotic heparin biocompatible copolymer conjugate may be applied directly over the first layer using the solvent evaporation method or other appropriate method. After the solvent is evaporate from the surface of an implantable medical device, a thin film of comprising anti-thrombotic heparin-bioabsorbable polymer conjugate is formed on the outmost surface. Alternatively the comb-type anti-thrombotic biocompatible copolymer may be processed into microsphere or nanosphere forms that also contain a drug before added to a drug eluting medical device.

The following examples illustrate the creation of the conjugate and uses in accordance with the principle of the present invention.

I. EXAMPLE 1

Preparation of a Comb-Type Biodegradable PLA Via a Ring Opening Polymerization of a Lactone Dimers (Lactide) with Poly(Vinyl Alcohol, PVA) as the Initiator As shown in FIG. 1, a pre-determined amount of d,l-lactide (from Purac, USA) is transferred to a dried round bottom glass reactor equipped with a magnetic stir bar. A pre-determined amount of poly(vinyl alcohol), (e.g. fully hydrolyzed Elvanol 70-03 from Du Pont, Inc.) and Stannous Octoate (Sigma, St. Louis, USA) are added to the glass reactor. The glass reactor is then sealed with a stopper and cycled three times between an argon gas and vacuum to remove the air and oxygen inside the reactor. The sealed reactor is then gradually heated to 140 C. under vacuum and kept stirred with the magnetic stir bar. Upon completion of the reaction, the polymer is dissolved in methylene chloride and precipitated in methanol and dried under vacuum and low heat.

II. EXAMPLE 2

Preparation of Comb-Type Anti-Thrombotic Heparin-Bioabsorbable Polymer Conjugate As shown in FIG. 2, a comb-type PLA, such as created in accordance with Example 1 above, is dissolved in anhydrous dimethylformamide (DMF), followed by dissolution of succinic anhydride and dicyclohexylcarbodiimide (DCC). The resulting solution is kept for 5 hours at room temperature under vacuum. The byproduct, dicyclohexylurea (DCU), and unreacted DCC and NHS are removed by filtration. The resultant intermediate is then re-precipitated in methanol and dried in vacuum oven. The carboxylic acid end caped intermediate is then activated by addition of N-hydroxylsuccinimide (NHS) in dimethylformamide and further reacted with heparin for 4 hours at room temperature to make the final comb type conjugate of comb type biodegradable polymer-heparin conjugate of the present invention. The final conjugate is precipitated and freeze-dried.

III. EXAMPLE 3

Coating of a Drug Eluting Stent with an Outmost Layer Comprising a Comb-Type Absorbable Polymer-Heparin Conjugate As shown in FIG. 3, the surface 10 of a cobalt chromium stent is spray coated with a drug containing polymeric solution, which may comprise for example, ethyl acetate (EA) containing PLGA and rapamycin. The weight ratio between PLGA and rapamycin is 2:1. After the drug-containing layer 20 is dried, a coating solution containing a comb-type absorbable polymer-heparin conjugate is spray coated onto the first drug-containing layer 20. After the layer is dried, a thin film 30 containing the comb-type absorbable polymer-heparin conjugate is formed on the outmost surface.

Coatings such as those described above can be thin, typically 5 to 8 microns deep. The surface area of a device such as a stent, by comparison is very large, so that the entire volume of the beneficial agent has a very short diffusion path to discharge into the surrounding tissue. The resulting cumulative drug release profile is characterized by a large initial burst, followed by a rapid approach to an asymptote, rather than the desired "uniform, prolonged release," or linear release. It is often desired to vary the elution pattern of a therapeutic agent from a device such as a stent. In addition, it is also desired to vary the amount of agent at different locations along the device. This can be accomplished by placing an agent within a structural feature of the device.

Figure 5:
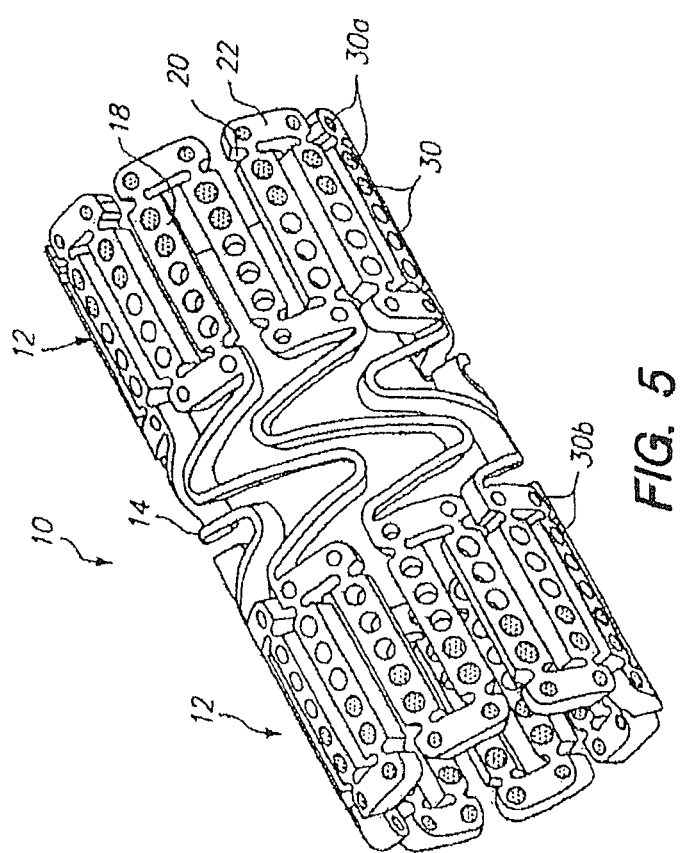
FIG. 5 is an isometric view of an expandable medical device with particles selectively placed into structural features of the device.

As shown in FIG. 5, an expandable device has a plurality of structural features that facilitate the placement of at least one agent on the device. The expandable medical device 10 illustrated in FIG. 5 may be cut from a tube of material to form a cylindrical expandable device. The expandable medical device 10 includes a plurality of cylindrical sections 12 interconnected by a plurality of bridging elements 14. The bridging elements 14 allow the device to bend axially when passing through the torturous path of vasculature to a deployment site and allow the device to bend axially when necessary to match the curvature of a lumen. A network of elongated struts 18 that are interconnected by ductile hinges 20 and circumferential struts 22 comprise the cylindrical tubes 12. During expansion of the medical device 10 the ductile hinges 20 deform while the struts 18 are not deformed. Further details of an example of the expandable medical device are described in U.S. Pat. No. 6,241,762 incorporated herein by reference in its entirety.

The elongated struts 18 and circumferential struts 22 include structural features such as openings 30, some of which are selectively filled with an agent for delivery to the lumen in which the expandable medical device is implanted. The depth of the openings 30 is dictated by the thickness of the struts 22. Other structural features may include raised sections or dimples, slits, elongated openings, added material and any feature that can capture or contain a material that is desired to be placed on the expandable device. In addition, other portions of the device 10, such as the bridging elements 14, may include structural features. In the particular example shown in FIG. 5, the openings 30 are provided in non-deforming portions of the device 10, such as the struts 18, so that the openings are non-deforming and the agent is delivered without risk of being fractured, expelled, or otherwise damaged during expansion of the device. A further description of one example of the manner in which the beneficial agent may be loaded within the openings 30 is described in U.S. Pat. No. 6,764,507 incorporated herein by reference in its entirety.

Figure 4:
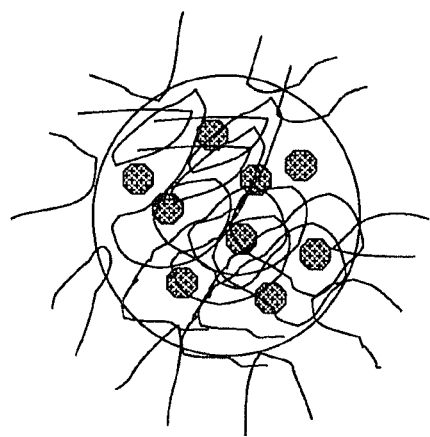
FIG. 4 is a schematic view showing a biodegradable comb type polyester heparin conjugate of the present invention first combined with a drug to form nanoparticles or microspheres.

In order to facilitate the placement of an agent or multiple agents within a structural feature of a device as shown in FIG. 5, a particle 40 can be created utilizing the comb type polymer and heparin conjugate as a carrier for the therapeutic agent as shown in FIG. 4. In this embodiment the agent 42 is somewhat associated with the hydrophobic core 46 of the comb polymer 44. The agent 42 is co-dissolved with the conjugate using a solvent that is later evaporated creating particles with the agent at their core. These particles are ideally suited for placement within the structure of a device such as illustrated in FIG. 5. For example, a device may have structural features such as wells, indentations, folds, or channels having particles therein. This allows for particles having differing properties to be placed at various locations along the device. Moreover, particles having at least two different agents can be located within the same structural feature. Agent is released from the structural feature as the particles degrade. Simultaneously, the presence of heparin will prevent thrombosis at the placement site of the device.

Figure 6:
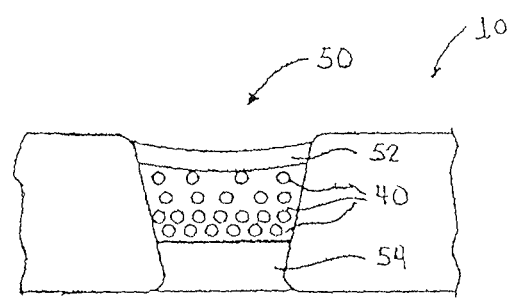
FIG. 6 is a cross sectional view of an expandable medical device having particles in accordance with the present invention in a first plurality of holes.

FIG. 6 illustrates a cross sectional view of an opening 50 in the device 10 of FIG. 5. A plurality of particles 40 is placed between two layers 52 and 54. Layers 52 and 54 can be varied in composition and thickness to control the exposure of particles 40 to an aqueous environment. This will control the release of agent from within the core of the particles 40. Additionally, the particles can be blended within a single material and placed within opening 50 of device 10.

Examples of methods for the formation of nanoparticles and microparticles for placement on or within a structural feature of a device are given below.

IV. EXAMPLE 4

Formation of Nanoparticles Using a Comb-Type Absorbable Polymer-Heparin and Paclitaxel Twenty mg of Paclitaxel and 200 mg of poly(lactide-toglycolide), PLGA50/50, are dissolved 16 ml of methylene chloride with gentle stirring. The formed solution is transferred to 250 ml of aqueous solution containing 4% of (polyvinyl alcohol) (PVA) as an emulsifier. The combined solution is sonicated with an energy output of 50 mW in a pulsed mode of a sonicator for 90 seconds. The emulsion is then stirred overnight at room temperature to remove the solvent. This forms nanospheres containing paclitaxel that are collected by centrifugation at 12000 rpm for 30 min and further washed with deionized water 4 times to remove excess emulsifiers. The product is then freeze-dried before application.

V. EXAMPLE 5

Formation of Microparticles Using a Comb-Type Absorbable Polymer-Heparin and Paclitaxel Twenty mg of Paclitaxel and 200 mg of poly(lactide-toglycolide), PLGA50/50, are dissolved 16 ml of ethyl acetate (EA) with gentle stirring. Eighty ml of water (water for injection grade) is heated up to 50 C and kept stirred by a magnetic stirring plate. A predetermined amount of emulsifier (PVA, 0.4 g) is added to form an aqueous solution. The solution is then cooled to room temperature under constant stirring. Ethyl acetate (3.2 ml) is added to the aqueous solution under gentle stirring. Paclitaxel and PLGA solution is then slowly poured to the emulsified aqueous solution that is being stirred at 500 rpm. The emulsion is further stirred for 4 hours at room temperature to solidify the microspheres. The final microspheres are then collected by filtration and washed 2 times with WFI water. The final microspheres are freeze-dried over night before subsequent use.

FIG. 4 shows particles made in accordance with the above-examples placed within an opening of the device shown in FIG. 5. The particles may be placed within these openings by a dry powder deposition method such as an electrostatic deposition process. These particle containing device may be further process to modulate the release kinetics of the drug with a process such as a solvent spray process to further modulate the release kinetics the opening may also be covered by additional coverings to adjust the release kinetics of the drug.

Although the present invention has been described above with respect to particular preferred embodiments, it will be apparent to those skilled in the art that numerous modifications and variations can be made to these designs without departing from the spirit or essential attributes of the present invention. Accordingly, reference should be made to the appended claims, rather than to the foregoing specification, as indicating the scope of the invention. The descriptions provided are for illustrative purposes and are not intended to limit the invention nor are they intended in any way to restrict the scope, field of use or constitute any manifest words of exclusion.

What is claimed is:

1. An apparatus comprising:
   a frame expandable from a first diameter to a second diameter wherein the frame has an inner surface and an outer surface, the distance between the surfaces defining the wall thickness of the frame;
   a plurality of structural features disposed along the frame; and
   a plurality of polymer anti-thrombotic conjugate particles situated with the plurality of structural features, wherein the anti-thrombotic conjugate comprises a biocompatible, bioabsorbable, hydrophobic polymer backbone having hydrophilic, antithrombotic end groups configured as an amphiphilic structure, the material having the following structure:

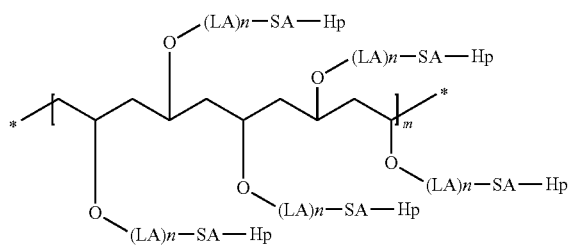

wherein n is an integer of 2-1000; and m is an integer of 100 to 5000; LA is repeating unit of lactic acid; SA is succinic acid; Hp is unmodified heparin conjugated to the material, the lactic acid, the succinic acid and the unmodified heparin form an integral part of the amphiphilic material the overall structure being comb-like in shape.

2. The apparatus of claim 1 wherein the plurality of structural features comprise ridges disposed on the surface of the frame.

3. The apparatus of claim 1 wherein the plurality of structural features comprises a plurality of wells formed in the frame.

4. The apparatus of claim 3 wherein the wells extend from the outer surface to the inner surface.

5. The apparatus of claim 3 wherein the plurality of wells is filled with the particles.

6. The apparatus of claim 1 wherein the plurality of polymer anti-thrombotic conjugate particles serves as a carrier for a therapeutic agent.

7. The apparatus of claim 1 wherein the plurality of particles comprises micro-particles.

8. The apparatus of claim 1 wherein the plurality of particles comprises nano-particles.

9. The apparatus of claim 1 further comprising an anti-thrombotic coating applied to the surface of the frame.

* * * * *